United States Patent [19]

Pompei Katz de Warrens

[11] 4,140,990

[45] Feb. 20, 1979

[54] PROBE FOR SELECTIVELY DETECTING VAPORS, WATER VAPOR IN PARTICULAR

[75] Inventor: Jean Pompei Katz de Warrens, Noisy-le-Roi, France

[73] Assignee: U.S. Philips Corporation, New York, N.Y.

[21] Appl. No.: 767,565

[22] Filed: Feb. 10, 1977

[30] Foreign Application Priority Data

Feb. 18, 1976 [FR] France .................... 76 04428

[51] Int. Cl.² ............... G01N 27/46; G01N 27/60; G01N 27/00
[52] U.S. Cl. ............... 338/35; 204/195 W; 324/29; 324/71 R; 324/158 P
[58] Field of Search ........... 204/1 W, 195 W, 195 R; 324/29, 71 R, 158 P; 338/35

[56] References Cited

U.S. PATENT DOCUMENTS

| | | | |
|---|---|---|---|
| 3,223,609 | 12/1965 | Reeds | 204/195 W |
| 3,954,590 | 5/1976 | Czuha | 204/195 W |

*Primary Examiner*—G. L. Kaplan
*Attorney, Agent, or Firm*—Bernard Franzblau

[57] ABSTRACT

A probe for selectively detecting a vapor component in a gaseous atmosphere in contact therewith. The probe includes a pair of measuring electrodes and a semiconductor layer which is coated with a dielectric layer. An auxiliary electrode is placed opposite the semiconductor layer so that the voltage can be varied and consequently the level of the average current can be adjusted. It is thereby possible to detect the concentration of a vapor component to be measured in the entire range and with the same sensitivity.

11 Claims, 6 Drawing Figures

PROBE FOR SELECTIVELY DETECTING VAPORS, WATER VAPOR IN PARTICULAR

The present invention relates to a probe for selectively detecting at least one vaporous component in a gas, the operation being based on variations in the impedance at the active surface of the probe under the influence of variations in the concentration of said component. The probe consists of a substrate on which there are two mutually separated electrode layers which are connected to a voltage source and a layer of semiconductor material covers both electrode layers. On top of the semiconductor layer is a coating of a dielectric material, at least a portion of the surface of said last coating constituting the active surface.

The invention relates in particular to the detection of polar molecules, for example water molecules. These polar molecules are able to form a surface charge on the dielectric materials in which they are retained by adsorption.

In a non-limitative embodiment the invention relates to a probe for detecting water vapor in air.

In a prior U.S. Pat. No. 4,025,892 there is described a probe of the above-mentioned type. The vaporous particles to be detected are adsorbed at the dielectric layer and produce on this layer a surface charge which induces a charge of opposite sign at the interface between the dielectric coating and the semiconductor layer. This causes a change to occur in the impedance of the surface of the semiconductor layer. The effect becomes stronger as the density of the relevant charges becomes greater and with uniform charge densities this effect depends on the thickness of the dielectric coating.

The probe according to the older patent application excels by virtue of its extraordinary sensitivity, high speed of response and very low energy consumption.

A disadvantage, however, is the very wide range of the impedance of the probe which, for example, for a given embodiment, may extend from some hundred ohms to several thousands of megaohms. In an embodiment of a probe for detecting water vapor in air which comprises a thin layer of zinc oxide coated with a film of tetraethoxysilane and which is operated with a constant voltage, the impedance measured in dry air is in the order of several tens of megaohms whereas at a humidity of 100% the impedance amounts to 1500 ohms, the intermediate scale varying exponentially.

Owing to the fact that the impedance value extends over such a wide range it is difficult to adapt the probe to the electronic part of the measuring device when the entire range of moisture values has a substantially uniform sensitivity. If one wants to measure or control the moisture content within the entire range of the scale, a plurality of probes having different sensitivities must be available or the amplifier section of the device must be modified.

The above-mentioned drawback also applies of course to probes for detecting other vaporous components.

It is an object of the invention to mitigate the drawback described above.

The invention provides a probe by means of which it is possible to measure or control concentrations within the entire range with an optimum sensitivity and reproduceability.

The probe of the type described above is characterized in that it is also provided with a third electrode which is disposed opposite the layer of semiconductor material and is in contact with at least the layer of dielectric material. By means of the third electrode a control voltage can be provided which is superimposed on the induced voltage that is present owing to the adsorbed molecules at the dielectric surface. As a consequence, the level of the measuring current can be set at will so that the measuring current is only variable within rather narrow limits. This obviates all problems as regards connecting the probe to the amplifier.

The flexibility in matching the impedance of the probe with three electrodes according to the invention signifies a very important advantage relative to the prior art probe with two electrodes. With a moisture detection probe it is, for example, possible to select, by setting the control voltage $V_c$ of the third electrode, i.e. the "control electrode," to a given value, the entire range of values of the humidity extending from 0 to 100%, per sector of usage which for example ranges from 0 to 10%, from 10 to 20%, from 20 to 30%, etc.

Another advantage of the probes according to the invention compared with the known probe provided with only two electrodes consists in a greater accuracy and an improved reproduceability of the measurements, especially at the beginning and at the end of the concentration scale, that is to say at the very low and the very high contents of the vapor to be detected in the gas. At these extreme values the impedance of a probe with two electrodes is either very high (several tens of megaohms) or very low (some hundreds of ohms). Especially with the very high impedance values the measuring accuracy is low. With a probe having three electrodes according to the invention this drawback is obviated by supplying a given control voltage to the third electrode. In this way the probe is adjusted to an impedance range which is outside the range of the extreme values mentioned above, and independent of the actual content of the vapor in the ambient atmosphere to be analyzed.

The probe according to the invention retains all of the advantages of the prior art probe. It has a high sensitivity, especially owing to the large surface-/volume ratio of the active part thereof and of the thin layer structure of the composite elements. On the other hand the energy consumption of this probe is low (in the micro ampère range at 8 to 10 Volts) which avoids warming it up relative to the environment and contributes towards the reliability of the measurements.

It should also be noted that the probe according to the invention is simple in construction.

A first embodiment of a probe according to the invention is manufactured by first applying the two measuring electrodes onto a substrate, thereafter the two electrodes are applied in an overlapping manner on the thin layer of semiconductor material. Thereafter the layer of dielectric material is placed on the semiconductor layer, and finally, the third (control) electrode is applied on the dielectric layer. The layer of dielectric material preferably covers the entire surface of said semiconductor layer and partially extends across the two measuring electrodes. The control electrode consists, for example, of a thin metal strip which is substantially parallel with the direction of the current lines through the semiconductor layer.

In accordance with a variant of the embodiment of the probe according to the invention the third electrode is deposited directly onto the semiconductor layer and consequently the film of dielectric material covers this third electrode.

Depending on whether said third electrode is disposed either on or under the dielectric layer the control voltage should be of opposite polarity in circumstances which are otherwise identical to obtain the same effect.

The material of the semiconductor layer is, for example, a binary compound of a metal and metalloid. This layer can also be applied by means of cathode sputtering. Preferably the layer of dielectric material consists of a metal organic compound, such as tetraethoxysilane; said layer can be obtained by polycondensation of the monomer in a glow discharge. The control electrode preferably consists of aluminum as this metal adheres perfectly to the tetraethoxysilane and does not diffuse when it is in direct contact with the material of the semiconductor layer.

Preferably the geometry of the two measuring electrodes on the substrate is chosen such that the capacitance between these two electrodes is as low as possible. As a result the probe functions in an optimum way when it is supplied with direct current. In this way it is possible to avoid, in certain critical cases, comb-shaped electrodes which are often used in associated embodiments.

Experiments proved that for a proper operation of the probe it is recommended that the surface area on or under the dielectric layer and occupied by the third electrode should not be higher than 45 to 50% of the common surface between the dielectric layer and the semiconductor layer.

The invention will be further explained and illustrated by means of examples and the accompanying drawings in which.

Figure 1:
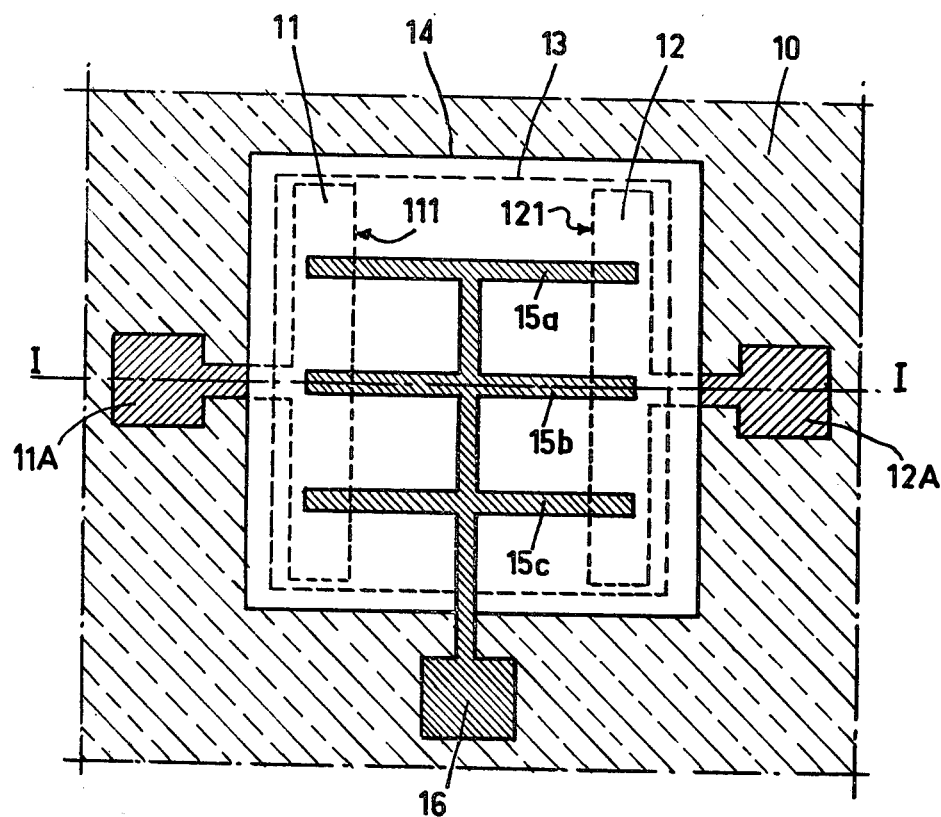
FIG. 1 is an elevational view of an embodiment of a probe for detecting vaporous components according to the invention.

The probe according to the invention is manufactured on a solid dielectric substrate, indicated by reference numeral 10 in the FIGS. 1, 2, 2a, 3 and 3a, for example a glass plate of the thickness of window glass.

Disposed on the substrate 10 are two thin conducting areas 11 and 12, for example in the form of rectangular surfaces, which constitute the measuring electrodes of the probe. These two areas consist, for example, of a layer of a nickel-chromium alloy.

On the areas 11 and 12 (the connecting lugs 11A and 12A excepted) and on the surrounding portions of the substrate 10 there is a thin layer of semiconductor material 13, for example stannic dioxide.

Figure 2:
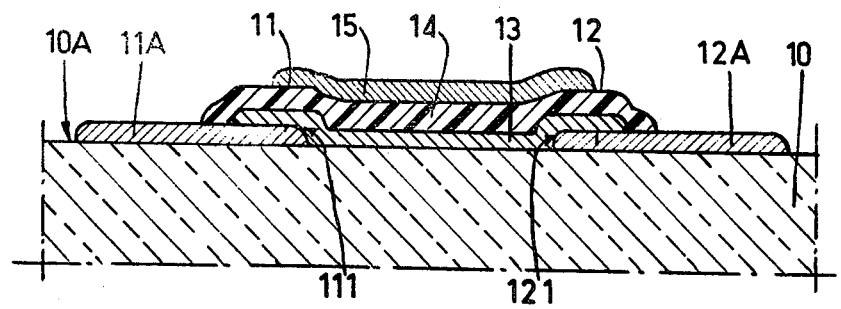
FIG. 2 is a cross-section of the same probe along the line I—I of FIG. 1.

In a first embodiment of the probe according to the invention FIGS. 1 and 2 as shown in said layer 13 is covered with a layer of dielectric material 14, for example tetraethoxysilane, the surface of this layer 14 constituting the detection plane of said probe. In accordance with the invention the probe is provided with a third electrode, or control electrode, 15, which in this embodiment is supported by the layer 14 and which extends across the substrate 10 by means of its connecting lug 16.

As FIG. 1 shows the electrode 15 is provided with three narrow branches 15a, 15b, 15c which are disposed parallel with and at substantially equal distances from one another in a direction which is parallel with the current lines through the layer 13. This construction of the electrode 15 is only meant as an example. This electrode may have any desired form provided that on the one hand the surface thereof is small relative to that of the layers 14 and 13, and that on the other hand the average direction of the elements thereof is substantially parallel with said current lines.

Preferably the length of the electrode 15 (in the present case the length of each of the elements 15a, 15b and 15c) is at least equal to the spacing between the electrodes 11 and 12, with spacing is measured between the opposite edges 111 and 121 thereof.

In the construction described the surface in the rectangular space between the electrodes 11 and 12, which is occupied by the semiconductor layer 13, is 12.5 mm$^2$, the spacing between said electrodes, which are approximately 5 mm long, from edge 111 to edge 121 is 2.5 to 5 mm, the branches 15a, 15b and 15c of the electrode 15 are 0.5 to 0.6 $\mu$m wide. In addition, the electrodes 11, 12 and 15 are 0.3 $\mu$m thick; the layer 13 is 0.06 $\mu$m thick and the layer 14 is 2 $\mu$m thick. These dimensions are, for example, those of a probe for controlling the atmospheric humidity.

Figure 3:
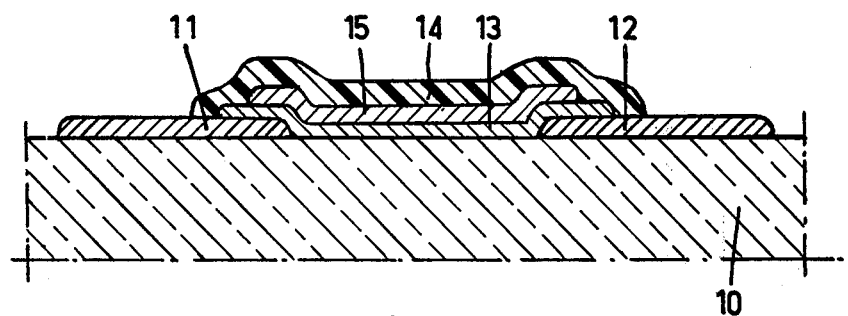
FIG. 3 is a cross-section of a variant of a construction of the probe according to FIG. 1 and FIG. 2.

The probe shown in FIG. 3 differs from that shown in FIG. 2 in that the electrode 15 is not located on the surface of the layer 14 but is placed between the layers 14 and 13. The direct contact between the elements 13 and 15 renders it necessary that the electrode 15 consist of an inert metal, for example aluminum, to prevent the electrical characteristic of the semiconductor layer from being changed.

Figure 2A:
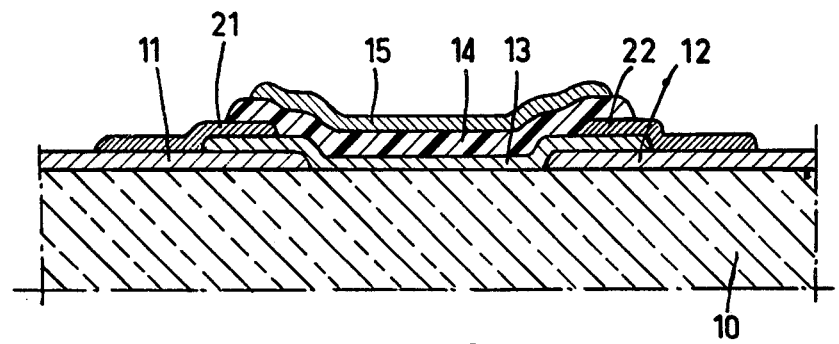
FIGS. 2a and 3a are cross-sections of an improved variant of the constructions shown in the FIGS. 2 and 3.
Figure 3A:
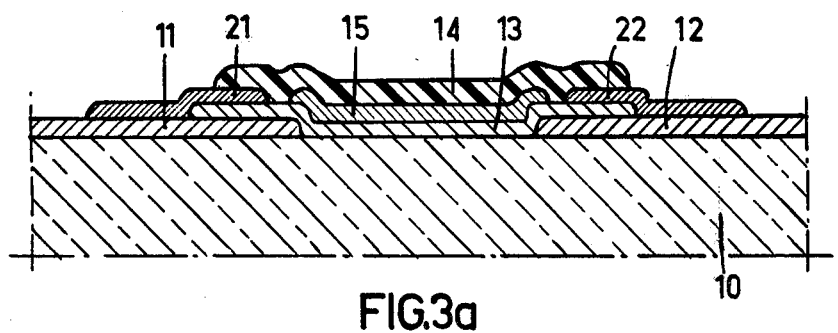

In the constructions of the probe as shown in FIGS. 2a and 3a the electrodes 12, 22 constitute jaws which surround the semiconductor layer 13 and build a contact therewith on both sides. This construction, in which the electrodes are disposed on either side of the semiconductor layer is advantageous in the case where the probe is supplied with a d.c. voltage between the electrodes 11 and 12.

The fabrication of the probe of FIG. 3a is slightly simpler than that of FIG. 2a because the electrode 15 and the conducting areas 21 and 22 can be applied simultaneously, at least when they consist of the same metal or the same alloy.

Applicants have ascertained that the maximum sensitivity of a probe according to the invention is obtained when the layers 13 and 14 are formed in an ionized environment.

The fabrication of a probe will be described for the construction as shown in FIGS. 1 and 2.

The coatings 11 and 12 consisting of a nickel chromium alloy are applied to a glass plate 10 by vacuum deposition from a wire of a nickel-chromium alloy (80% nickel, 20% chromium). Thereafter the layer is chemically etched in accordance with the pattern chosen for the areas 11 and 12.

The substrate 10, which now is provided with the claddings 11 and 12, is then placed on an aluminum receiving electrode of a cathode sputtering arrangement, the target plate electrode of which is a nickelplated steel plate with a target plate of solid tin or of tin powder.

The target plate electrode and the receiving electrode are 80 mm apart.

The discharge atmosphere is dry air the pressure of which is maintained at $0.5 \cdot 10^{-2}$ Torr. The supply voltage is a d.c. voltage of 2.5 kV.

In these circumstances a discharge current is produced of 1.60 mA per cm$^2$ surface area of the target plate and a thin layer 13 of stannic oxide is deposited on the substrate 10, which layer has stable oxygen deficiencies, the rate of growing being 0.08 μm per minute.

After formation of the layer 13 it is coated with a dielectric layer of tetraethoxysilane by means of the same cathode sputtering arrangement.

When the sputtering room is empty, vapor of the monomer of tetraethoxysilane is fed into this space to a pressure of $10^{-3}$ to $10^{-2}$ Torr. Condensation then occurs in various points of the room and, particularly, on the bare area of the structure before the discharge is initiated.

To avoid condensation on the target plate which would result in arcs prior to the discharge said target plate electrode must be heated slightly (45 to 55° C.), for example by hot air circulation.

A glow discharge is then induced between the target plate electrode and the receiving electrode so that an additional deposit of monomer is formed on said area, at the same time that polymerization of the coating formed begins. The duration of the discharge in a pure atmosphere of tetraethoxysilane is 2.5 to 3 minutes.

Thereafter the vapor of the monomer is gradually replaced by oxygen without stopping the discharge and by maintaining the pressure at the same time between $10^{-3}$ and $10^{-2}$ Torr. Replacement lasts for approximately 3 minutes during which period the polymerization of the tetraethoxysilane is continued. After the replacement has finished the discharge is continued for another 1 - 1¼ minute in order to form a silicon oxide layer at the surface of the tetraethoxysilane film to protect the silane in the layer which has not yet been polymerized and which would evaporate upon exposure to the air.

The spacing between the receiving electrode and the target plate electrode must be at least 150 mm as otherwise the deposited tetraethoxysilane will be damaged by the ion bombardment. The d.c. voltage applied between said electrodes is 1.5 kV so that the discharge current is approximately 1.5 mA per cm$^2$ of the surface of the target plate electrode or the receiving electrode.

Polymerization of the tetraethoxysilane coating is completed by heating the substrate at 300° C. for approximately 1 hour in an oxygen atmosphere, for example air, at a normal atmosphere. Finally, the electrode 15 is applied. Preferably this electrode consists of aluminum which is obtained by vacuum-coating through a suitable mask. Heating the silane coating for polymerization can be performed after application of electrode 15. This is the sole possibility when the electrode 15 is placed between the oxide layer 13 and the layer 14.

In the case where probes are fabricated like those shown in FIGS. 2a and 3a, applying the conducting areas 21 and 22 must be introduced at a suitable stage in the range of operations described above.

Figure 4:
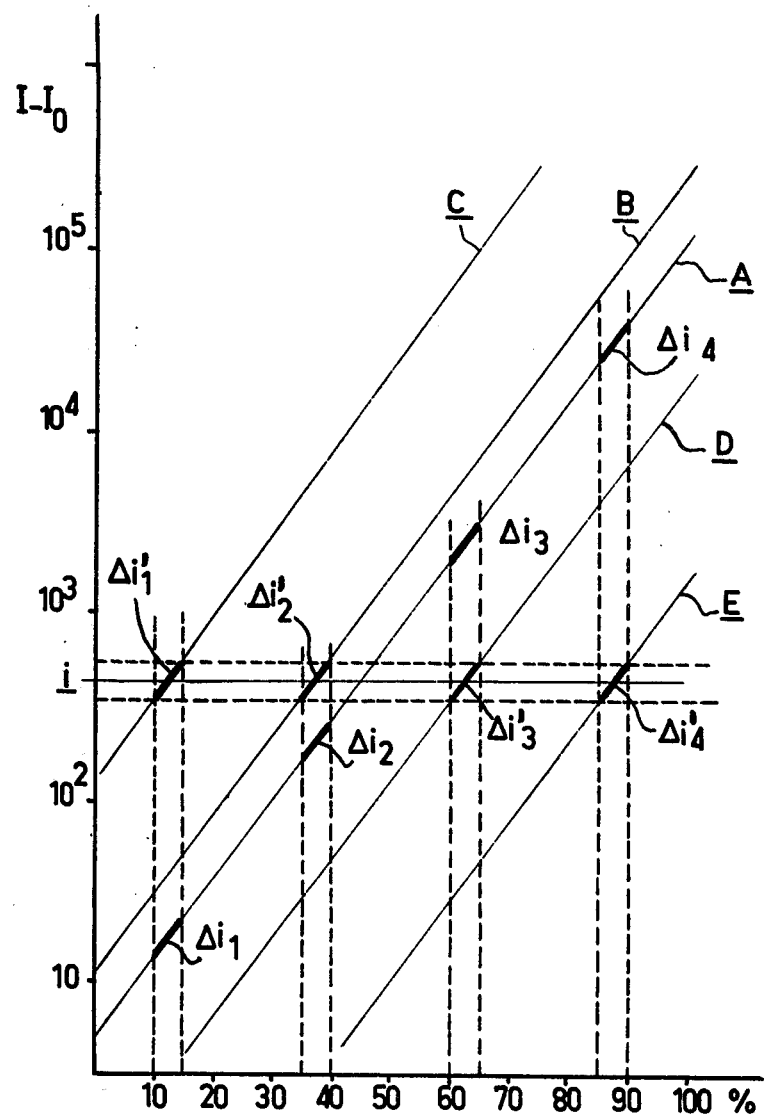
FIG. 4 is a graph which represents, by means of a logarithmic scale, the current through a probe according to the invention for detecting water vapor in air as a function of the ambient humidity, and various control voltages on the third electrode.

The graph of FIG. 4 comprises five curves. These curves indicate the variations in the current through the probe according to the invention which is, for example, designed for controlling the humidity of air as a function of this humidity at different values of the voltage $V_c$ which is applied to the control electrode 15 of said probe.

The graph shows the current I-$I_o$ instead of the total current I, $I_o$ being the current at a value of $V_c = 0$ at the control electrode.

In view of the wide range of its possible values the current is shown on a relative scale in powers of 10, that is to say in a logarithmic scale, while the humidity is indicated in %.

The curve A of the graph corresponds with a probe which is fed with a constant voltage between its two electrodes 11 and 12, the voltage on the electrode 15 being zero, for example by connecting it to the chassis of the electronic apparatus which is connected to the probe.

The impedance of the probe at various degrees of humidity varies with the number of water vapor molecules which hit the detection area of the layer 14 and remain adsorbed there. As already indicated above, applicants assume that these water vapor molecules bring a charge on the layer 14, a positive charge in the present case, which induces a negative charge by means of capacitive action at the interface of the layer 14 and the semiconductor layer 13. This causes the impedance of said semiconductor layer to change.

The current variations as a function of the humidity of the air are plotted in a curve having a pronounced exponential variation, which is shown on a logarithmic axis in FIG. 4.

Applying an additional control voltage through the electrode 15 means a change in the charge which is induced at the surface of the layer 13 and which originally could only be attributed to water vapor molecules. In the graph this is indicated by a parallel shift to the right or to the left of the original curve with $V_c = 0$, depending on the value of $V_c$.

In the present case of the graph of FIG. 4 two values of the control voltage which are positive relative to the original value of the potential of the electrode 15 correspond with the straight lines B and C, whereas lines D and E apply for values of the control voltage at the electrode 15 which are negative relative to said original voltage. As discussed above it is possible to obtain by means of a voltage of a suitable value and polarity at the third electrode the situation that variations of the current through the probe, which correspond to changes in the humidity outside, occur around a chosen level of the current and independent of the value on the scale of the hygrometer. If the degree of humidity varies 5%, for example, between the value 10 and 15%, the straight line A shows that the current varies by $\Delta i_1$. The variation $\Delta i_1$ is indicated on the graph by means of a thicker line. In the same manner 5% changes in the degree of humidity between the values of 35 and 40%, thereafter between 60 and 65%, and finally between 85 and 90% cause variations $\Delta i_2$, $\Delta i_3$ and $\Delta i_4$ respectively, which are also plotted on the straight line A. It is clear that the average levels of the current I - $I_o$ around which said variations $\Delta i_1$, $\Delta i_2$, $\Delta i_3$ and $\Delta i_4$ are located are very remote one another owing to the rapid increase in said current with the humidity. In the considered case the observation was at all times limited to the straight line A. It will be seen that the current at a humidity of 85 to 90% is at least $10^3$ times greater than the current at a humidity of 10 to 15%.

As, by means of a suitable control voltage applied to the electrode 15, the straight line A is replaced by the straight line C, the range from 10 to 15% of the value of the humidity now corresponds to the variation $\Delta i'_1$ which is indicated by means of thick solid lines on the straight line C. This variation is displaced to the level I of the current I-$I_o$. Likewise the variations $\Delta i_2$, $\Delta i_3$, $\Delta i_4$ can be replaced by the variations $\Delta i'_2$, $\Delta i'_3$, $\Delta i'_4$, which have all been displaced to the level of the value i thanks to a proper choice of the control voltage at electrode 15.

In practice a probe according to the invention is used preferably with a voltage V which is between 0.1 and 10 Volts, depending on the spacing between the measuring electrodes while the voltage $V_c$ which is applied to the control electrode varies within 3 Volts. Consequently it is possible with this probe and a proper amplifier to measure each level of the hygrometer scale with a proper accuracy.

I claim:

1. A probe for selectively detecting at least one vapourous component in a gas in contact with the probe, the operation of the probe being based on variations in its electric impedance due to a reaction at an active surface of the probe under the influence of variations in the concentration of said component, said probe comprising, a substrate on which two measuring electrode layers are disposed, said two electrode layers being separated from one another and being adapted for connection to a voltage source, a layer of semiconductor material covering the two electrode layers and on top thereof a layer of dielectic material, at least a portion of the surface of said dielectric layer constituting said active surface, and a third electrode disposed opposite the semiconductor material layer and which is at least in contact with the layer of dielectric material.

2. A probe as claimed in claim 1, wherein the third electrode comprises one or more elongate elements, at least one of the elements of the third electrode being disposed substantially parallel with the direction of current lines which in operation will pass through the thin layer of semiconductor material from the one to the other of the two measuring electrodes.

3. A probe as claimed in claim 2 wherein said one element of the third electrode is at least as long as the minimum spacing, viewed perpendicularly, between the edges of said two first measuring electrodes.

4. A probe as claimed in claim 1 wherein the surface of the third electrode is at the most equal to half the common surface between the dielectric layer and the semiconductor layer.

5. A probe as claimed in claim 1 wherein the third electrode is disposed at the outer side on the dielectric layer opposite the semiconductor layer.

6. A probe as claimed in claim 1 wherein the third electrode is disposed between the dielectric layer and the semiconductor layer.

7. A probe as claimed in claim 1 wherein said semiconductor layer is comprised of stannic oxide, the dielectric layer comprises tetraethoxysilane and the third electrode comprises aluminum.

8. A probe as claimed in claim 1 wherein said two electrode layers comprise parallel elongate strip-shaped elements with the third electrode extending generally perpendicular thereto and said third electrode is adapted to be connected to a source of control voltage.

9. A probe as claimed in claim 1 wherein the layer of semiconductor material and the layer of dielectric material are formed on the substrate in an ionized environment.

10. A probe for selectively detecting at least one component of a gas in contact with the probe, the operation of the probe being based upon the variation of its electrical impedance due to a reaction at an active surface of the probe, said probe comprising, a dielectric substrate, a pair of spaced apart measuring electrodes disposed on the substrate and each having terminal means for connection to a voltage source, a layer of semiconductor material on said substrate and covering the measuring electrodes, a layer of dielectric material on top of the semiconductor layer, at least a part of the dielectric layer forming said active surface of the probe, and a third electrode disposed opposite the semiconductor layer and in contact with the layer of dielectric material for applying a control voltage thereto whereby the level of current flow can be adjusted.

11. A probe as claimed in claim 10 wherein the third electrode comprises a thin strip-shaped conductive element sandwiched between the semiconductor layer and the dielectric layer.

* * * * *